(12) United States Patent
Ruthenberg et al.

(10) Patent No.: US 11,596,544 B2
(45) Date of Patent: Mar. 7, 2023

(54) GAS BUBBLE REMOVAL FOR ENDORECTAL COOLING DEVICES

(71) Applicant: Profound Medical Inc., Mississauga (CA)

(72) Inventors: Raymond Matthew Ruthenberg, Toronto (CA); Ting On Wong, Oakville (CA)

(73) Assignee: Profound Medical Inc., Mississauga (CA)

( * ) Notice: Subject to any disclaimer, the term of this patent is extended or adjusted under 35 U.S.C. 154(b) by 598 days.

(21) Appl. No.: 16/684,880

(22) Filed: Nov. 15, 2019

(65) Prior Publication Data

US 2021/0145635 A1    May 20, 2021

(51) Int. Cl.
| | |
|---|---|
| *A61F 7/12* | (2006.01) |
| *A61F 7/02* | (2006.01) |
| *A61F 7/00* | (2006.01) |

(52) U.S. Cl.
CPC .............. *A61F 7/12* (2013.01); *A61F 7/02* (2013.01); *A61F 2007/0028* (2013.01); *A61F 2007/0064* (2013.01); *A61F 2007/0239* (2013.01); *A61F 2007/126* (2013.01)

(58) Field of Classification Search
CPC .............................. A61F 7/12; A61F 2007/126
See application file for complete search history.

(56) References Cited

U.S. PATENT DOCUMENTS

| | | | |
|---|---|---|---|
| 8,679,147 B2 | 3/2014 | Isham | |
| 9,498,274 B2 * | 11/2016 | Burnett | ............ A61B 17/12022 |
| 10,271,889 B2 | 4/2019 | Bronskill et al. | |
| 2009/0018446 A1 | 1/2009 | Medan et al. | |
| 2016/0193076 A1 | 7/2016 | Moffitt et al. | |

FOREIGN PATENT DOCUMENTS

| | | |
|---|---|---|
| CA | 2826761 C | 8/2018 |
| EP | 2585012 B1 | 11/2020 |

OTHER PUBLICATIONS

ISA, "International Search Report", PCT/IB2019/001227, dated Jul. 3, 2020.

* cited by examiner

*Primary Examiner* — Kaitlyn E Smith
(74) *Attorney, Agent, or Firm* — Intrinsic Law Corp.

(57) ABSTRACT

An endorectal cooling device (ECD) includes an elongated body, a cooling fluid circuit, and a gas bubble removal device. The elongated body includes an insertable portion for insertion into a patient's rectum and an external portion that remains external to the rectum. The cooling fluid circuit is defined in the elongated body from the external portion to the insertable portion and circulates cooling fluid to regulate a temperature of a cooling surface on the insertable portion. The gas bubble removal device can include a coil, a tube, a mesh, and/or a hole that is disposed on or defined in the insertable portion of the elongated body, such as the cooling surface. A low-pressure source, such as a vacuum pump or a Venturi structure, can be fluidly coupled to the gas bubble removal device to remove fluid and bubbles by a suction force after the ECD is inserted into the rectum.

23 Claims, 8 Drawing Sheets

GAS BUBBLE REMOVAL FOR ENDORECTAL COOLING DEVICES

TECHNICAL FIELD

This application generally relates to devices for controlling the temperature of a body cavity and surrounding tissue, and more particularly, to devices for controlling the temperature in the context of thermal therapy applied to an organ or tissue that is proximal to the cavity.

BACKGROUND

During thermal treatment of the prostate, energy is delivered from an energy-delivery device to eliminate or reduce the diseased cells in the prostate. An unwanted side effect of heating the diseased tissue can be over-heating adjacent non-diseased tissue and organs. For example, in the thermal therapy of the prostate, the rectum and other healthy tissues near the prostate can be heated beyond what is safe or healthy for the patient. It is desired to limit the thermal dose or maximum temperature applied to these tissues, such as the rectal wall proximal to the prostate.

Endorectal cooling devices (ECDs) can be used to maintain the temperature of the rectum and surrounding tissue at a safe level. These devices generally include an elongated body and an internal fluid circuit. An example of an ECD is disclosed in U.S. Patent Application Publication No. 2016/0193076, titled "Endocavity Temperature Control Device," published on Jul. 7, 2016, which is hereby incorporated by reference.

Figure 1:
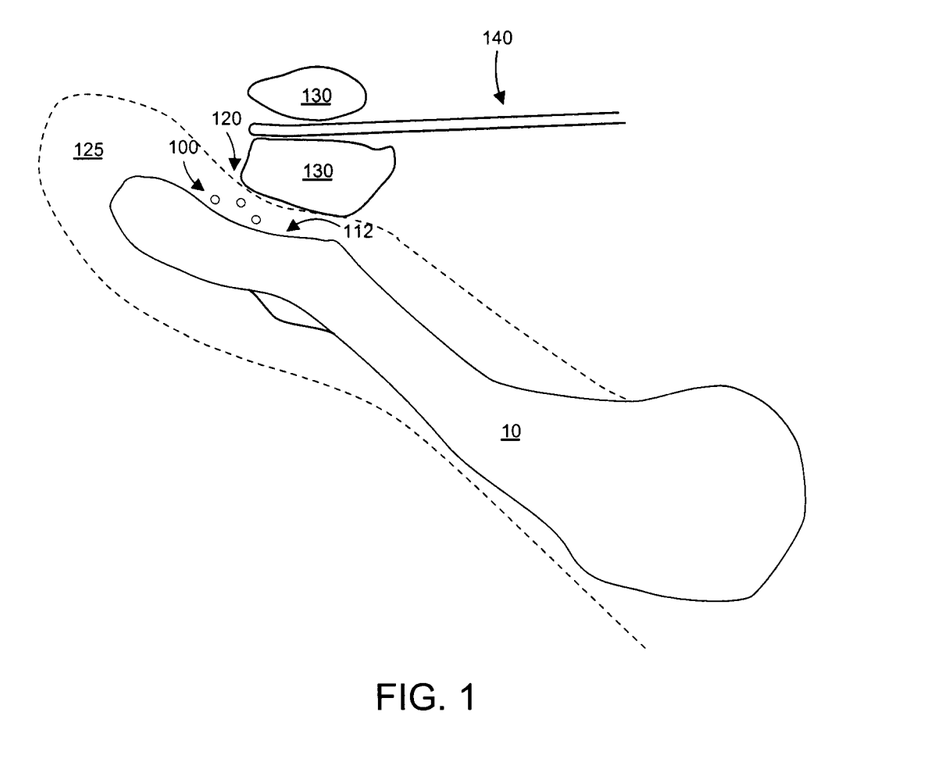
FIG. 1 illustrates an endorectal cooling device (ECD) according to the prior art.

When existing ECDs are inserted into the rectum, a volume of air is introduced into the rectal cavity to form gas bubbles (e.g., air bubbles). The gas bubbles rise in the rectal cavity and become disposed between the ECD and the rectal wall proximal to the prostate. In addition, gas bubbles from intestinal gases naturally exist in the rectal cavity and behave similarly to the gas bubbles formed during ECD insertion. For example, FIG. 1 illustrates gas bubbles 100 disposed between the cooling surface 112 of ECD 10 and the rectal wall 120 of rectum 125 proximal to prostate 130. For purpose of this illustration and for clarity, the distance between the ECD's cooling surface 112 and the rectal wall 120 is illustrated as larger than it is in practice. In operation, the ECD's cooling surface 112 is disposed proximal or adjacent to the rectal wall 120, and gas bubbles 100 becomes trapped therebetween. For completeness, FIG. 1 illustrates a thermal applicator 140 inserted transurethrally through the upper and lower portions of prostate 130. These gas bubbles reduce the effectiveness of the ECD by impeding the heat transfer between the ECD and the rectal wall. Gas bubbles also create an acoustic impedance which can reflect ultrasound energy and affect tissue heating.

To remove the gas bubbles 100, the ECD 10 can be swept side to side.

It would be desirable to reduce or eliminate the gas bubbles in the rectal cavity.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

An aspect of the invention is directed to an endorectal cooling device (ECD) comprising: an elongated body having an insertable portion for insertion into a rectum of a patient and an external portion that remains external to the rectum, the insertable portion having an external cooling surface; a cooling fluid circuit in the elongated body that extends from the external portion to the insertable portion, the cooling fluid circuit circulating a cooling fluid to regulate a temperature of the cooling surface; and a gas bubble removal means disposed on or defined in the cooling surface.

In one or more embodiments, the gas bubble removal means comprises a tube or a coil disposed on the cooling surface. In one or more embodiments, the tube or the coil is fluidly coupled to a vacuum pump, and at least one hole is defined in the tube or the coil. In one or more embodiments, the at least one hole is aligned with a rectal wall proximal to a prostate. In one or more embodiments, the gas bubble removal means comprises the coil, and the coil is wrapped around an insertable portion of the ECD in a spiral.

In one or more embodiments, the gas bubble removal means comprises the tube, and the tube comprises a loop of tubing. In one or more embodiments, the loop of tubing is elongated along an axis that is parallel to a length of an insertable portion of the ECD. In one or more embodiments, the ECD further comprises a plurality of the loops disposed laterally from each other along the cooling surface.

In one or more embodiments, the gas bubble removal means comprises a mesh structure disposed in a gap in the cooling surface. In one or more embodiments, the mesh structure is fluidly coupled to a vacuum pump via a tube. In one or more embodiments, the gas bubble removal means comprises a plurality of holes defined in the cooling surface, and the holes are fluidly coupled to a low-pressure source via a gas bubble removal channel, the gas bubble removal channel defined in a housing of the ECD.

Another aspect of the invention is directed to an endorectal cooling device (ECD) comprising: an elongated body having an insertable portion for insertion into a rectum of a patient and an external portion that remains external to the rectum, the insertable portion having an external cooling surface; a gas bubble removal channel defined in the elongated body; a plurality of holes defined in the cooling surface, the holes extending from the cooling surface to the gas bubble removal channel; a low-pressure source fluidly coupled to the holes via the gas bubble removal channel; and a cooling fluid circuit defined in the elongated body, the cooling fluid circuit in thermal communication with the cooling surface.

In one or more embodiments, the low-pressure source comprises a Venturi structure that is formed in a proximal end of the elongated body. In one or more embodiments, the low-pressure source comprises a vacuum pump.

In one or more embodiments, the cooling fluid circuit comprises a cooling fluid channel that extends in a loop from a proximal end to a distal end of the elongated body. In one or more embodiments, a portion of the cooling fluid channel is disposed between the cooling surface and the gas bubble removal channel. In one or more embodiments, an internal wall defines each hole, the internal wall extending to the gas bubble removal channel such that the holes are only fluidly coupled to the gas bubble removal channel. In one or more embodiments, each internal wall forms a cone that defines each hole.

In one or more embodiments, the ECD further comprises an ultrasound coupling fluid channel defined in the elongated body, the ultrasound coupling fluid channel extending from the proximal end to the distal end of the elongated body. In one or more embodiments, an outlet of the ultrasound coupling fluid channel is disposed adjacent a distal end of the cooling surface. In one or more embodiments, an ingress portion of the cooling fluid channel is between the ultrasound coupling fluid circuit and the gas bubble removal channel. In one or more embodiments, the gas bubble removal channel is between the ingress portion of the cooling fluid and an egress portion of the cooling fluid.

BRIEF DESCRIPTION OF THE DRAWINGS

For a fuller understanding of the nature and advantages of the present concepts, reference is made to the following detailed description of preferred embodiments in connection with the accompanying drawings.

DETAILED DESCRIPTION

A gas bubble removal device is disposed on or defined in the ECD's external cooling surface, which is disposed proximal to the prostate when the ECD is inserted into a patient's rectum. The gas bubble removal device includes one or more features for removing gas bubbles after the ECD is inserted into the patient's rectum.

In some embodiments, the gas bubble removal device includes a coil or a tube (in general, coil) that is disposed on the ECD's external cooling surface. The gas bubble removal coil causes a gap to form between the ECD's cooling surface and the rectal wall proximal to the prostate. In addition, the gas bubble removal coil can provide an irregular path for the gas bubbles to travel, which is energetically more favorable than the smooth ECD external surface. In some embodiments, the gas bubble removal coil can be fluidly coupled to a vacuum pump to remove the gas bubbles. For example, the gas bubble removal coil can include one or more holes that is/are aligned with the rectal wall proximal to the prostate. A vacuum can be applied to the gas bubble removal coil which causes fluid, including the gas bubbles, to enter the hole(s) and flow through the coil to an external fluid reservoir.

In another embodiment, the gas bubble removal device includes a mesh structure disposed on the ECD's external cooling surface. For example, the mesh structure can form a portion of the ECD's external cooling surface. Alternatively, the mesh structure can form a portion of the ECD's housing. The mesh structure is fluidly coupled to a vacuum pump (e.g., via one or more tubes) to remove the gas bubbles. A vacuum can be applied to the mesh structure which causes fluid, including the gas bubbles, to flow through the mesh structure to an external fluid reservoir (e.g., via one or more tubes).

In another embodiment, the gas bubble removal device includes a plurality of holes defined in the ECD's external cooling surface and/or housing. The holes are fluidly coupled to a first end of a gas bubble removal channel. A low-pressure source, such as a vacuum pump or a Venturi structure, is fluidly coupled to a second end of the gas bubble removal channel. The low-pressure source causes fluid and gas bubbles to flow through the holes and the gas bubble removal channel for collection in an external reservoir.

In some embodiments, the gas bubble removal device includes a combination of two or more of the features described above. For example, the gas bubble removal device can include a combination of any of the coil, tube, mesh, and/or holes.

In some embodiments, ultrasound-visible markers can be disposed on the ECD that allow the ECD to be visible with ultrasound imaging. In addition, the ECD can include an ultrasound coupling fluid channel that introduces ultrasound coupling fluid between the ECD and the rectal wall. Additionally or alternatively, the ECD can include a cooling fluid circuit that circulates cooling fluid in the ECD to cool and/or regulate the temperature of the cooling surface to thereby cool and/or regulate the temperature of the rectal wall and surrounding anatomy.

Figure 2:
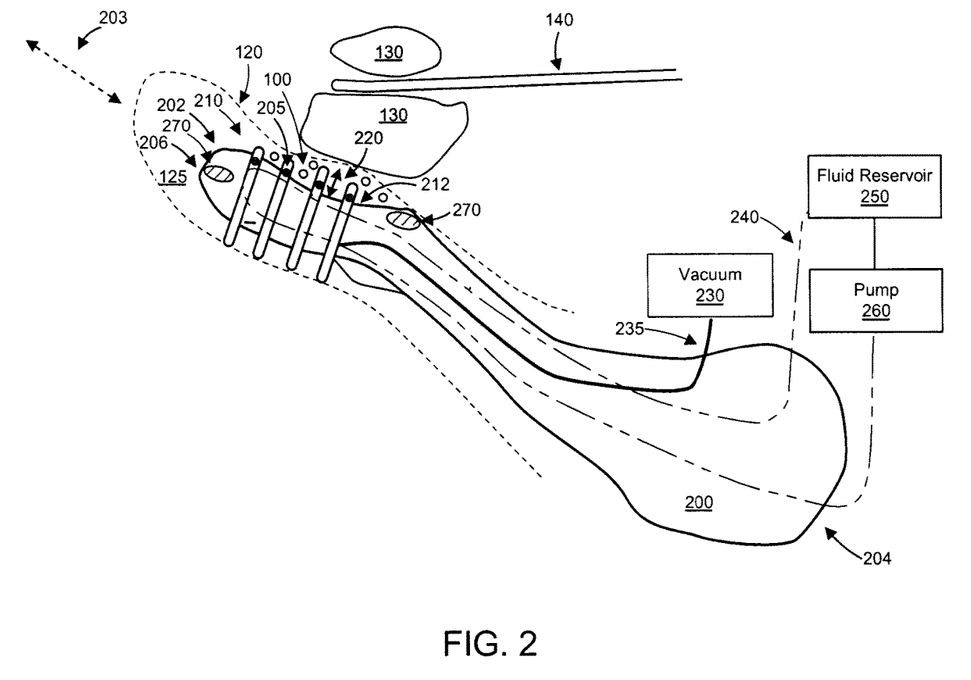
FIG. 2 illustrates an elongated ECD having a gas bubble removal coil according to one or more embodiments.

FIG. 2 illustrates an elongated ECD 200 having a gas bubble removal coil 210 according to one or more embodiments. The gas bubble removal coil 210 is wrapped around an insertable portion 202 of ECD 200 in a spiral manner. For example, the gas bubble removal coil 210 has a central axis that is generally parallel to an axis 203 that defines the length of the insertable portion 202. When the insertable portion 202 is inserted into the rectum 125, the gas bubble removal coil 210 is disposed between the rectal wall 120 and the ECD's cooling surface 212 (e.g., on the housing of ECD 200) in a gap 220 therebetween. The gas bubble removal coil 210 can provide a surface along which the gas bubbles 100 can travel to escape that is energetically preferable to the smooth cooling surface 212 of the ECD 200. The gas bubble removal coil 210 can comprise a single tube or multiple tubes. For example, multiple tubes can be disposed next to each other and run in parallel to form the gas bubble removal coil 210. Alternatively, multiple tubes can be connected (e.g., serially) end-to-end to form the gas bubble removal coil 210.

The coil 210 includes one or more optional holes 205 that is/are in fluid communication with a vacuum pump 230 or other low-pressure source to extract the gas bubbles 100. In the embodiment where the gas bubble removal coil 210 includes multiple tubes disposed next to each other, one, some or all of the tubes can include a hole 205, and such tube(s) can be in fluid communication with the vacuum pump 230. The holes 205 can be distributed along the length of the coil 210 or they can be disposed only in certain portions of the coil 210. The vacuum pump 230 can be powered electrically or manually. In some embodiments, the vacuum pump 230 is disposed on or in the housing of the ECD 200. A vacuum tube 235 fluidly couples the vacuum pump 230 to the coil(s) 210. The vacuum tube 235 can be disposed on the exterior surface of the ECD 200 and/or in a chamber or channel that extends through the ECD 200.

A cooling fluid circuit 240 circulates cooling fluid through the ECD 200. The cooling fluid circuit 240 includes a cooling fluid reservoir 250 and a pump 260 for circulating the cooling fluid through the cooling fluid circuit 240. The cooling fluid circuit 240 can extend from a proximal end 204 to a distal end 206 of the ECD 200 including through the insertable portion 202. The cooling fluid circuit 240 can pass proximally to the cooling surface 212 so that the cooling fluid is in thermal communication with the cooling surface 212 to reduce and/or regulate the temperature thereof, and thus to reduce and/or regulate the temperature of the rectal wall 120 and nearby patient anatomy.

The ECD 200 also includes optional ultrasound-visible markers 270. The ultrasound-visible markers 270 have a higher acoustic impedance than the housing of the ECD 200, which allows them to be visible using ultrasound. For example, the ultrasound-visible markers 270 can comprise titanium or another high-acoustic-impedance material.

Figure 3:
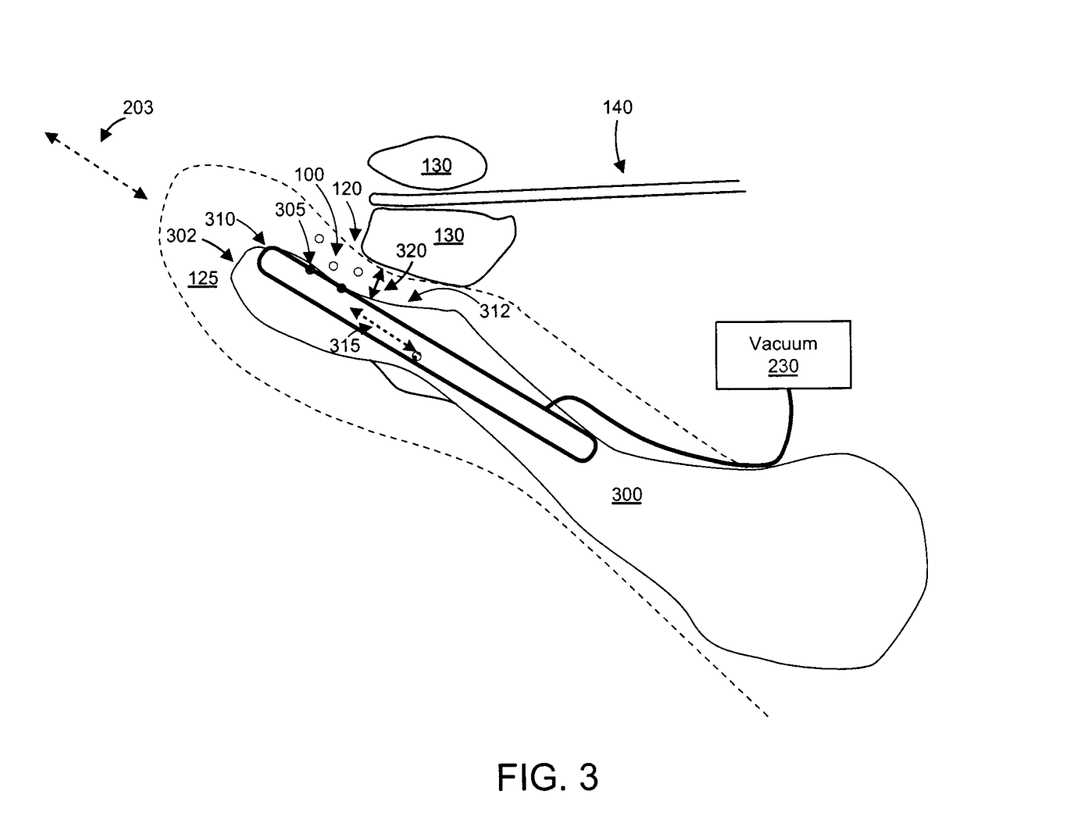
FIG. 3 illustrates an example of an elongated ECD having a gas bubble removal coil according to an alternative embodiment.

FIG. 3 illustrates an example of an elongated ECD 300 having a gas bubble removal tube 310 according to an alternative embodiment. The tube 310 is disposed partially or fully on the external surface of an insertable portion 302 of the ECD 300. The tube 310 comprises an elongated loop of tubing that extends along at least a portion of the length of the ECD 300. For example, the tube 310 can form a rectangular or oval shape that is elongated along an axis 315 that is parallel to axis 203. In some embodiments, the tube 310 can include two or more loops. For example, a first loop can be disposed inside a second loop (i.e., the first loop is wider, such as along an axis that is orthogonal to axis 315, than the second loop such that the first loop fits within the second loop). Alternatively, the first and second loops can be disposed adjacent or laterally from each other along the cooling surface 312 of the ECD 300. In another embodiment, a plurality of loops can be disposed along the elongated length of the ECD 300 (e.g., along the cooling surface 312), for example in an end-to-end configuration or in an overlapping configuration.

When the ECD 300 is inserted into the rectum 125, at least some of the tube 310 is disposed between the rectal wall 120 and the ECD's cooling surface 112 (e.g., on the housing of ECD 110) in a gap 320 therebetween. The tube 310 can provide a surface along which the gas bubbles 100 can travel to escape that is energetically preferable to the smooth cooling surface 312 of the ECD 300.

One or more of the loops in tube 310 can include one or more holes 305 that is/are in fluid communication with a vacuum pump 230 to extract the gas bubbles 100, for example as described above with respect to coil 210. The ECD 300 can include ultrasound-visible markers such as ultrasound-visible markers 270. In addition or in the alternative, the ECD 300 can include a cooling fluid circuit such as cooling fluid circuit 240, which is not illustrated in FIG. 3 for clarity purposes only.

Figure 4:
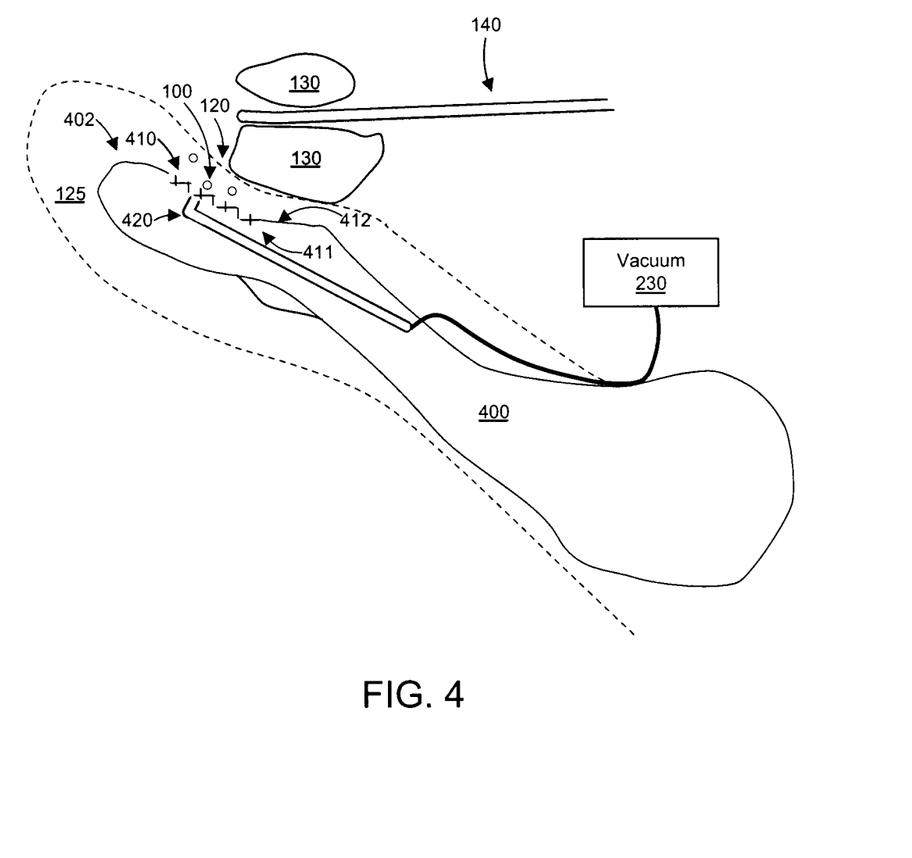
FIG. 4 illustrates an example of an elongated ECD having a mesh or porous material for removing gas bubbles according to an alternative embodiment.

FIG. 4 illustrates an example of an elongated ECD 400 having a mesh or porous material 410 for removing gas bubbles according to an alternative embodiment. The mesh or porous material 410 is disposed in a gap 411 of the cooling surface 412 in the insertable portion 402 of the ECD 400 such that the mesh or porous material 410 faces the rectal wall 120 when the ECD 400 is inserted into the rectum 125. The mesh or porous material 400 provides a surface along which the gas bubbles 100 can travel to escape that is energetically preferable to the smooth cooling surface 412 of the ECD 400. In addition, the gas bubbles 100 can flow through the mesh or porous material 410 and into an internal or external channel 420 when a vacuum is applied by vacuum pump 230. In some embodiments, the channel 410 is an internal channel that can be fluidly coupled (e.g., via a manifold) to other channels in the ECD 400, such as for circulating cooling fluid. In some embodiments, the mesh or porous material 410 comprises a woven plastic sheet or a woven fabric.

The ECD 400 can include ultrasound-visible markers such as ultrasound-visible markers 270. In addition or in the alternative, the ECD 400 can include a cooling fluid circuit such as cooling fluid circuit 240, which is not illustrated in FIG. 4 for clarity purposes only.

Figure 5:
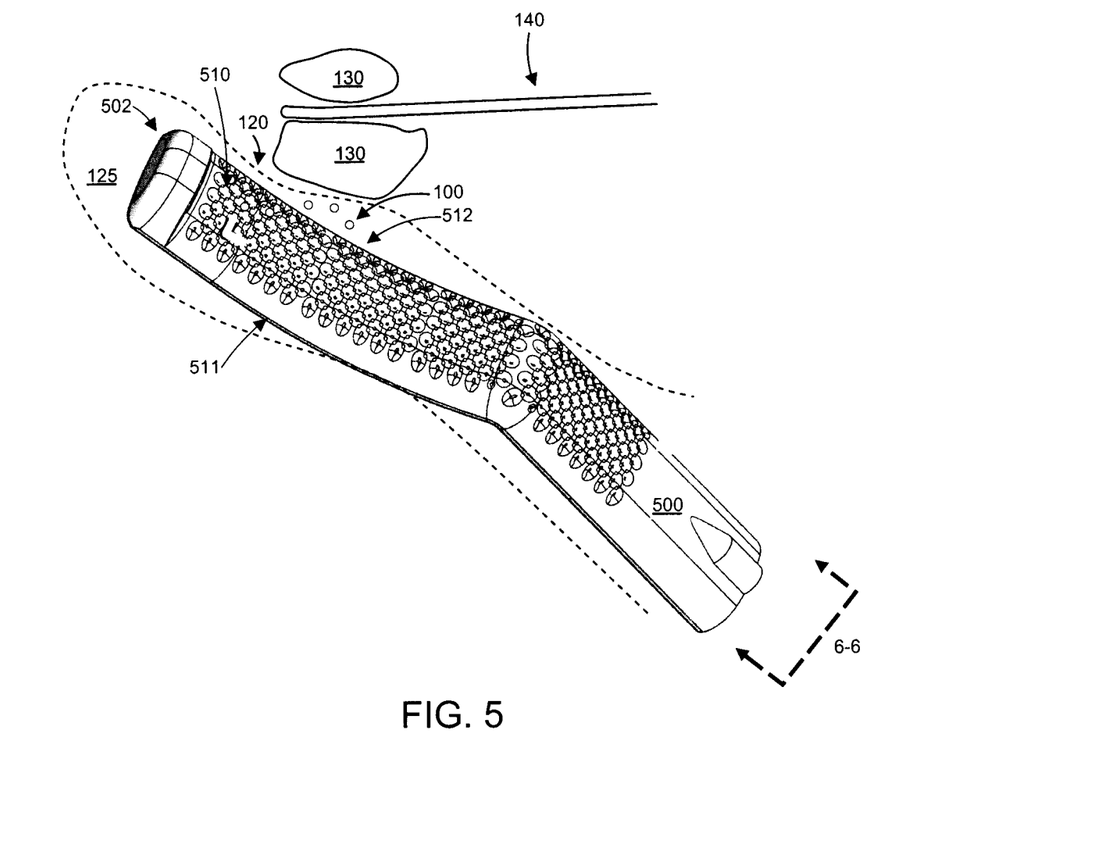
FIG. 5 illustrates an example of an elongated ECD having a plurality of holes for removing gas bubbles according to an alternative embodiment.

FIG. 5 illustrates an example of an elongated ECD 500 having a plurality of holes 510 for removing gas bubbles according to an alternative embodiment. The holes 510 are defined in the housing 511 on the insertable portion 502 of the ECD 500 such as in cooling surface 512 and/or other portions of the elongated body. The holes 510 can be disposed in a regular or irregular arrangement. For example, the holes 510 can be disposed in an array, a pattern, or another regular arrangement. Alternatively, the holes 510 can be disposed irregularly in the housing 511. Regardless of the arrangement, the holes 510 can have the same sizes and/or different sizes. For example, the holes can have (a) the same and/or different widths (e.g., diameters) and/or (b) the same and/or different cross-sectional profiles. In some embodiments, the holes 510 can be formed by 3D printing.

The holes 510 are fluidly coupled to a low-pressure source such that fluid in the rectum 125, and any bubbles 100 in the fluid, is drawn through the holes 510 to one or more channels that extend(s) between the holes 510 and the low-pressure source.

Figure 6:
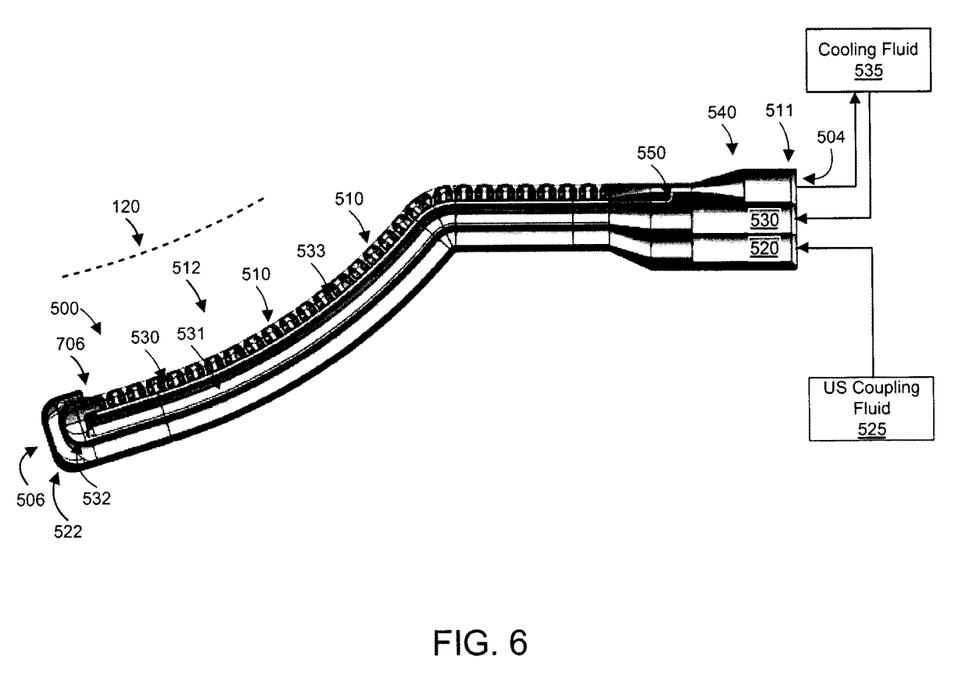
FIG. 6 illustrates a cross section of the ECD illustrated in FIG. 5.

FIG. 6 is a cross-section of ECD 500 through plane 6-6 in FIG. 5. As illustrated in FIG. 6, ECD 500 includes a plurality of channels defined in the housing 511. For example, an ultrasound coupling fluid channel 520 is a first channel defined in the housing 511 and extends from a proximal end 504 to a distal end 506 of the ECD 500. The proximal end 504 of the ultrasound coupling fluid channel 520 is fluidly coupled to an ultrasound coupling fluid reservoir 525 which can include a pump that causes the ultrasound coupling fluid to flow through the ultrasound coupling fluid channel 520 from the proximal end 504 to the distal end 506 of the ECD 500. Additionally or alternatively, the ultrasound coupling fluid reservoir 525 can be disposed higher than the ECD 500 to gravity feed the ultrasound coupling fluid into the ultrasound coupling fluid channel 520. The ultrasound coupling fluid can comprise a biocompatible liquid such as saline solution that has approximately the same acoustical impedance as the bodily fluids in the rectum 125, for example to minimize acoustic reflection or scatter.

At or near the distal end 506, the ultrasound coupling fluid channel 520 has a U-shaped bend 522 so that an outlet 524 of the ultrasound coupling fluid channel 520 is adjacent to a distal end 706 of the cooling surface 512. The outlet 524 is preferably configured so that the ultrasound coupling fluid generally flows parallel to or towards the cooling surface 512 so that at least some ultrasound coupling fluid contacts the cooling surface 512 and/or other surfaces of the ECD 500 to improve ultrasound imaging and thermal coupling of tissue to the ECD 500. In other embodiments, the ultrasound coupling fluid channel 520 can be configured so that the ultrasound coupling fluid is directed away from the cooling surface 512. For example, the outlet 524 can be configured so that the ultrasound coupling fluid is directed towards the rectal wall 120 and away from the cooling surface 512. In some embodiments, the flow or "current" of the ultrasound coupling fluid can move the bubbles towards the holes 510 or away from the cooling surface 512, which can be an advantage of the ECD 500 configuration. In other embodiments, the ultrasound coupling fluid channel 520 can include a first exit that directs the ultrasound coupling fluid parallel to the cooling surface 512 and a second exit that directs the ultrasound coupling fluid away from the cooling surface 512. The ultrasound coupling fluid provides an acoustic coupling medium to transfer ultrasound energy to and/or from the ECD 500, such as during ultrasound imaging to position the cooling surface 512 of the ECD 500 with respect to the rectal wall 120.

A cooling fluid channel 530 is a second channel defined in the housing 511 and extends from the proximal end 504 to the distal end 506 of the ECD 500 in a loop. At the proximal end 504, the cooling fluid channel 530 is fluidly coupled to a cooling fluid reservoir 535 which can include a pump that causes the cooling fluid to flow through the cooling fluid channel 530 from the proximal end 504 to the distal end 506 of the ECD 500. Additionally or alternatively, the cooling fluid reservoir 535 can be disposed higher than the ECD 500 to gravity feed the cooling fluid into the cooling fluid channel 530. The cooling fluid can comprise a biocompatible liquid such as saline solution that can transfer thermal energy to and/or from the cooling surface 512.

At or near the distal end 506, the cooling fluid channel 530 has a U-shaped bend 532 that redirects the cooling fluid back towards the proximal end 504 of the ECD 500. After the U-shaped bend 532, the cooling fluid channel 530 is disposed adjacent to the cooling surface 512 such that thermal energy can be transferred between the cooling surface 512 and the cooling fluid. At the proximal end 504, the cooling fluid channel 530 includes an optional Venturi structure 540 that causes a reduction in pressure, which can function as a vacuum pump to suck the ultrasound coupling fluid, entrained gas bubbles, and/or gas bubbles out of the interface between the rectal wall and the ECD and into the cooling fluid channel 530. The cooling fluid exiting the cooling fluid channel 530 can flow into the cooling fluid reservoir 535 for recirculation back through the cooling fluid channel 530. In some embodiments, the ultrasound coupling fluid and vacuum generating device are coupled to separate fluid circuits. In some embodiments, a heat exchanger can be disposed between the Venturi structure 540 and the cooling fluid reservoir 535 to reduce the temperature of the cooling fluid. In alternative embodiments, the Venturi structure 540 can be replaced with a vacuum pump, which can be disposed internally or externally with respect to the ECD 500.

In some embodiments, when the ultrasound coupling fluid and the cooling fluid comprise the same or compatible types of fluid (e.g., saline), the ultrasound coupling fluid channel 520 and the cooling fluid channel 530 can be combined at the proximal end 504 of the ECD 500 such that the ultrasound coupling fluid channel 520 and the cooling fluid channel 530 having a single inlet. The single inlet can be fluidly coupled to a single fluid reservoir, which can be the same as the ultrasound coupling fluid reservoir 525 or the cooling fluid reservoir 535. An internal wall that separates the ultrasound coupling fluid channel 520 and the cooling fluid channel 530 can be disposed between the proximal end 504 and the distal end 506 of the ECD 500. Alternatively, the internal wall can be disposed at or after the U-shaped bend.

A gas bubble removal channel 550 is a third channel defined in the housing 511 and extends from the proximal end 504 to the distal end 506 of the ECD 500. The gas bubble removal channel 550 is disposed between the ingress 531 and egress 533 portions of the cooling fluid channel 530. The gas bubble removal channel 550 is in fluid communication with the fluids and gas bubbles 100, disposed between the cooling surface 512 and the rectal wall 120, via the holes 510 which extend from the cooling surface 512 to the gas bubble removal channel 550. Near the proximal end 504, the gas bubble removal channel 550 merges with the cooling fluid channel 530. The low-pressure caused by the Venturi structure 540 causes fluids and gas bubbles 100 to flow through the holes 510 and out through the gas bubble removal channel 550.

Figure 7:
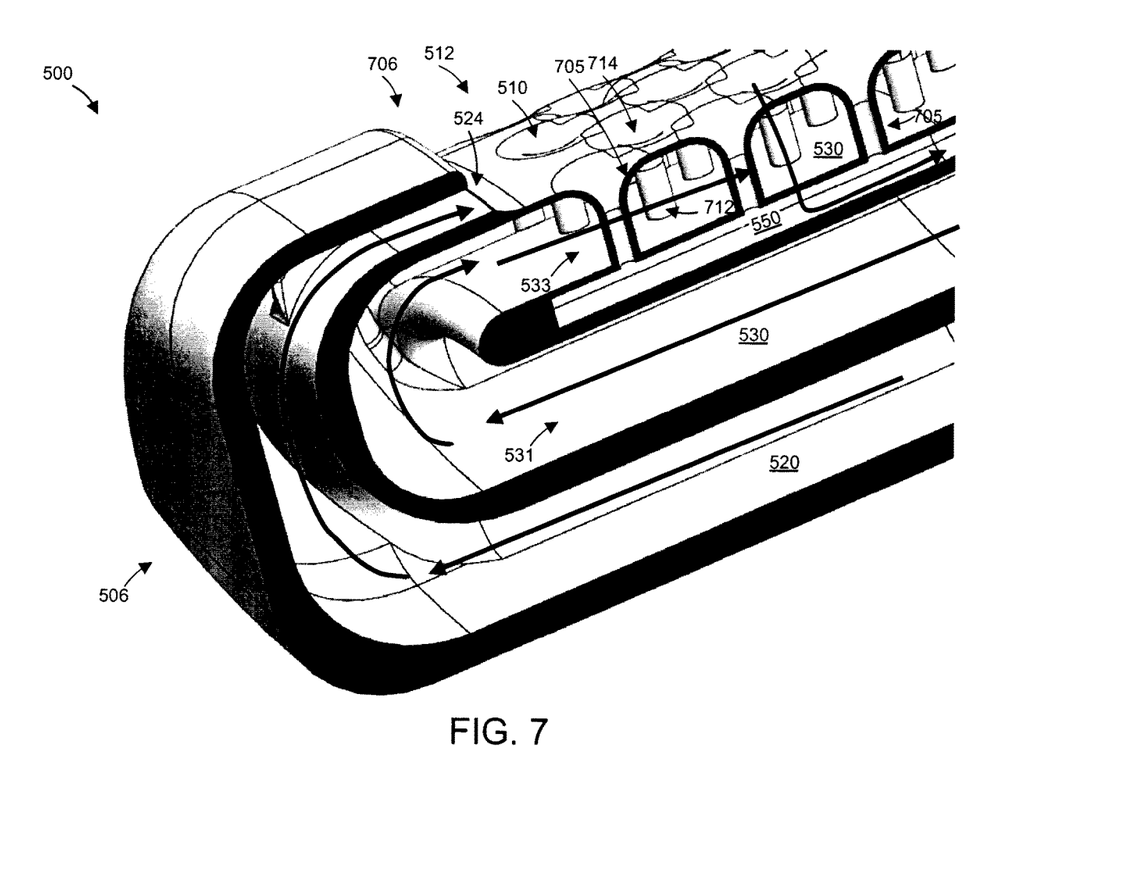
FIG. 7 is a detailed view of the cross-section illustrated in FIG. 6 at the distal end of the ECD.

FIG. 7 is a detailed view of the cross-section illustrated in FIG. 6 at the distal end 506 of the ECD 500. Representative arrows indicate the direction of fluid flow in the ultrasound coupling fluid channel 520, the cooling fluid channel 530, and the gas bubble removal channel 550. In addition, FIG. 7 illustrates that the holes 510 are defined by an internal wall 705 that forms optional cones 710 having a tube 712 that extends from a cone opening 714 to the gas bubble removal channel 550 through the egress 533 portion of the cooling fluid channel 530. The internal wall 705 fluidly couples the holes 510 to the gas bubble removal channel 550 but not to the cooling fluid channel 530. In other embodiments, some or all of the holes 510 can be formed by a tube, such as tube 712, without the cone opening 714. In addition or in the alternative, the cone opening 714 can have a rectangular or square cross section instead of a circular cross section. In addition or in the alternative, the tube 712 can have a rectangular or square cross section instead of a circular cross section.

Figure 8:
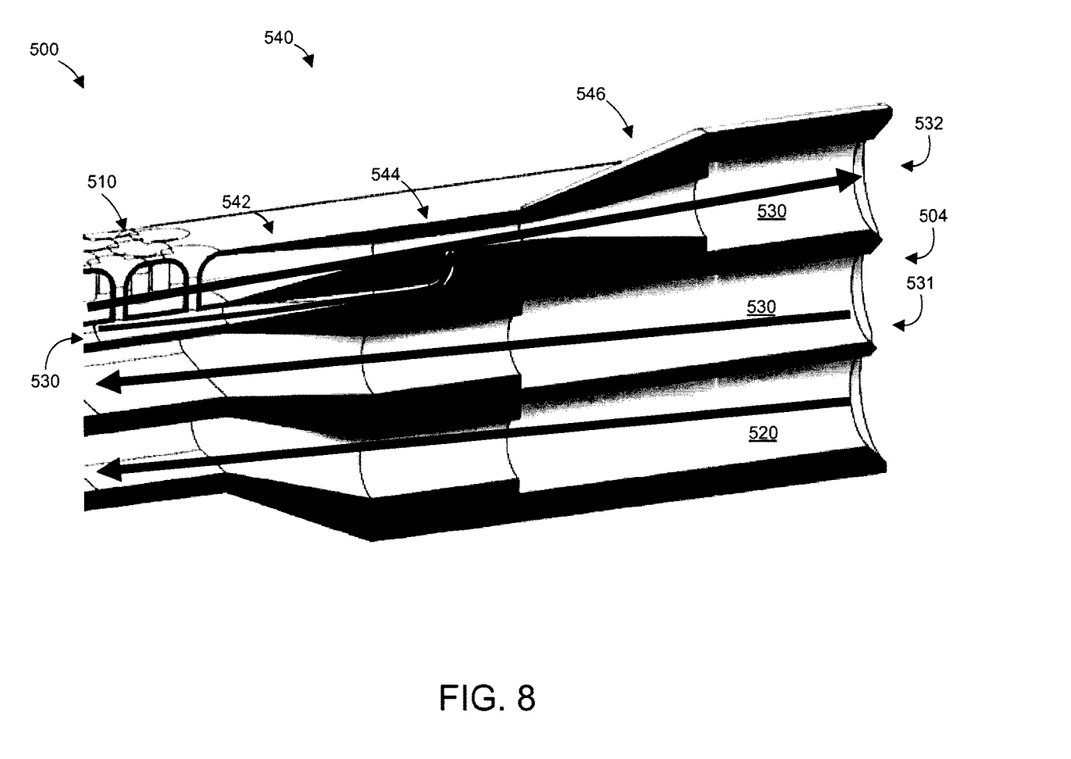
FIG. 8 is a detailed view of the cross-section illustrated in FIG. 6 at the proximal end of the ECD.

FIG. 8 is a detailed view of the cross-section illustrated in FIG. 6 at the proximal end 504 of the ECD 500. Representative arrows indicate the direction of fluid flow in the ultrasound coupling fluid channel 520, the cooling fluid channel 530, and the gas bubble removal channel 550. In addition, FIG. 8 illustrates that the Venturi structure 540 includes an inlet cone 542 having a tapered cross-sectional width for fluid flow, a generally cylindrical throat or neck 544 having a narrowed cross-section width for fluid flow, and an outlet cone 546 having an expanding cross-sectional width for fluid flow.

In some embodiments, the ECD 200, 300, and/or 400 can include an internal channel that introduces ultrasound coupling fluid between the respective ECD and the rectal wall 120, such as ultrasound coupling fluid channel 520.

The invention should not be considered limited to the particular embodiments described above, but rather should be understood to cover all aspects of the technology as fairly set out herein. Various modifications, equivalent processes, as well as numerous structures to which the invention may be applicable, will be apparent to those skilled in the art to which the invention is directed upon review of this disclosure.

The invention claimed is:

1. An endorectal cooling device (ECD) comprising:
an elongated body having an insertable portion for insertion into a rectum of a patient and an external portion that remains external to the rectum, the insertable portion having an external cooling surface;
a cooling fluid circuit in the elongated body that extends from the external portion to the insertable portion, the cooling fluid circuit circulating a cooling fluid to regulate a temperature of the external cooling surface; and
a gas bubble removal means disposed on or defined in the cooling surface, wherein:
the gas bubble removal means comprises a coil disposed on the external cooling surface,
the coil is fluidly coupled to a vacuum pump,
at least one hole is defined in the coil, and
the coil is wrapped around the insertable portion of the ECD in a spiral.

2. The ECD of claim 1, wherein the at least one hole is aligned with a rectal wall proximal to a prostate.

3. The ECD of claim 1, wherein:
the gas bubble removal means further comprises a tube disposed on the cooling surface,
the tube is fluidly coupled to the vacuum pump, and
the tube comprises a loop of tubing.

4. The ECD of claim 3, wherein the loop of tubing is elongated along an axis that is parallel to a length of the insertable portion of the ECD.

5. The ECD of claim 4, further comprising a plurality of the loops of the tubing disposed laterally from each other along the external cooling surface.

6. The ECD of claim 1, wherein the gas bubble removal means further comprises a mesh structure disposed in a gap in the external cooling surface.

7. The ECD of claim 6, wherein the mesh structure is fluidly coupled to the vacuum pump via a tube.

8. The ECD of claim 1, wherein:
the gas bubble removal means further comprises a plurality of holes defined in the external cooling surface, and
the holes are fluidly coupled to a low-pressure source via a gas bubble removal channel, the gas bubble removal channel defined in a housing of the ECD.

9. An endorectal cooling device (ECD) comprising:
an elongated body having an insertable portion for insertion into a rectum of a patient and an external portion that remains external to the rectum, the insertable portion having an external cooling surface;
a gas bubble removal channel defined in the elongated body;
a plurality of holes defined in the external cooling surface, the holes extending from the external cooling surface to the gas bubble removal channel;
a low-pressure source fluidly coupled to the holes via the gas bubble removal channel;
a cooling fluid circuit defined in the elongated body, the cooling fluid circuit in thermal communication with the external cooling surface; and
a coil disposed on the external cooling surface, the coil fluidly coupled to a vacuum pump, wherein at least one hole is defined in the coil, and the coil is wrapped around the insertable portion of the ECD in a spiral.

10. The ECD of claim 9, wherein the low-pressure source comprises a Venturi structure that is formed in a proximal end of the elongated body.

11. The ECD of claim 9, wherein the low-pressure source comprises the vacuum pump.

12. The ECD of claim 9, wherein the cooling fluid circuit comprises a cooling fluid channel that extends in a loop from a proximal end to a distal end of the elongated body.

13. The ECD of claim 12, wherein a portion of the cooling fluid channel is disposed between the external cooling surface and the gas bubble removal channel.

14. The ECD of claim 13, wherein an internal wall defines each hole, the internal wall extending to the gas bubble removal channel such that the holes are only fluidly coupled to the gas bubble removal channel.

15. The ECD of claim 14, wherein each internal wall forms a cone that defines each hole.

16. The ECD of claim 12, further comprising an ultrasound coupling fluid channel defined in the elongated body, the ultrasound coupling fluid channel extending from the proximal end to the distal end of the elongated body.

17. The ECD of claim 16, wherein an outlet of the ultrasound coupling fluid channel is disposed adjacent a distal end of the external cooling surface.

18. The ECD of claim 16, wherein an ingress portion of the cooling fluid channel is between the ultrasound coupling fluid circuit and the gas bubble removal channel.

19. The ECD of claim 18, wherein the gas bubble removal channel is between the ingress portion of the cooling fluid channel and an egress portion of the cooling fluid channel.

20. An endorectal cooling device (ECD) comprising:
an elongated body having an insertable portion for insertion into a rectum of a patient and an external portion that remains external to the rectum, the insertable portion having an external cooling surface;
a cooling fluid circuit in the elongated body that extends from the external portion to the insertable portion, the cooling fluid circuit circulating a cooling fluid to regulate a temperature of the external cooling surface; and
a gas bubble removal means disposed on or defined in the external cooling surface,
wherein:
the gas bubble removal means comprises a tube disposed on the external cooling surface,
the tube is fluidly coupled to a vacuum pump,
at least one hole is defined in the tube, and
the tube comprises a loop of tubing.

21. The ECD of claim 20, wherein the loop of tubing is elongated along an axis that is parallel to a length of the insertable portion of the ECD.

22. The ECD of claim 21, further comprising a plurality of the loops of the tubing disposed laterally from each other along the external cooling surface.

23. An endorectal cooling device (ECD) comprising:
an elongated body having an insertable portion for insertion into a rectum of a patient and an external portion that remains external to the rectum, the insertable portion having an external cooling surface;
a gas bubble removal channel defined in the elongated body;
a plurality of holes defined in the cooling surface, the holes extending from the external cooling surface to the gas bubble removal channel;
a low-pressure source fluidly coupled to the holes via the gas bubble removal channel;
a cooling fluid circuit defined in the elongated body, the cooling fluid circuit in thermal communication with the external cooling surface; and
a tube disposed on the external cooling surface, the tube fluidly coupled to a vacuum pump, wherein at least one hole is defined in the tube, and the tube comprises a loop of tubing.

* * * * *